United States Patent
Kamiya et al.

(10) Patent No.: US 7,307,739 B2
(45) Date of Patent: Dec. 11, 2007

(54) SYSTEM AND METHOD FOR DETECTING DROPPING AMOUNT OF LIQUID CRYSTAL

(75) Inventors: Hiroyuki Kamiya, Gyeonggi-do (KR); Duck-Jong Suh, Seoul (KR); Baek-Kyun Jeon, Gyeonggi-do (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 33 days.

(21) Appl. No.: 11/228,952

(22) Filed: Sep. 16, 2005

(65) Prior Publication Data

US 2006/0151727 A1   Jul. 13, 2006

(30) Foreign Application Priority Data

Jan. 13, 2005   (KR) .................. 10-2005-0003222

(51) Int. Cl.
*G01B 11/22* (2006.01)
*G02F 1/1341* (2006.01)

(52) U.S. Cl. ............... 356/627; 356/335; 250/577

(58) Field of Classification Search ........... 356/335, 356/627; 222/55
See application file for complete search history.

(56) References Cited

U.S. PATENT DOCUMENTS

| | | | |
|---|---|---|---|
| 4,935,261 A * | 6/1990 | Srivastava et al. ............ 427/10 |
| 5,739,432 A | 4/1998 | Sinha | |
| 5,938,643 A | 8/1999 | Lerner | |
| 6,285,421 B1 | 9/2001 | Lutnaes | |
| 6,590,650 B1 * | 7/2003 | Delahaye et al. ........... 356/335 |
| 6,851,784 B1 * | 2/2005 | Kietzmann .................... 347/19 |
| 6,992,746 B2 * | 1/2006 | Okuyama .................... 349/189 |
| 2002/0089561 A1 * | 7/2002 | Weitzel et al. ................ 347/19 |
| 2005/0083538 A1 * | 4/2005 | Arnold et al. ............. 356/627 |
| 2005/0170072 A1 * | 8/2005 | Kwak et al. .................. 427/58 |

FOREIGN PATENT DOCUMENTS

| | | |
|---|---|---|
| JP | 2003-295149 | 10/2003 |
| JP | 2004-122114 | 4/2004 |
| KR | 2001-0107968 | 12/2001 |
| KR | 1020020088219 | 11/2002 |

(Continued)

OTHER PUBLICATIONS

English Language Abstract, JP Patent First Publication No. 2003-295149, Oct. 15, 2003, 1 page.

(Continued)

*Primary Examiner*—Gregory J. Toatley, Jr.
*Assistant Examiner*—Rebecca C Slomski
(74) *Attorney, Agent, or Firm*—MacPherson Kwok Chen & Heid LLP

(57) ABSTRACT

A system for determining the amount of LC that is dropped on a display panel is presented. The system can adjust the amount of the LC to be dropped based on a real-time feedback on the amount of LC that is currently being dropped. The amount of LC that is being dropped is detected by utilizing a light source and a CCD camera. Because LC is not consumed wastefully and the detection interval is shortened with this system, the amount of LC that is dropped can be controlled more accurately and manufacturing cost is reduced.

11 Claims, 5 Drawing Sheets

FOREIGN PATENT DOCUMENTS

| KR | 1020030095813 | 12/2003 |
|---|---|---|
| KR | 1020030096512 | 12/2003 |
| KR | 1020040008966 | 1/2004 |
| KR | 1020040057946 | 7/2004 |

OTHER PUBLICATIONS

English Language Abstract, JP Patent First Publication No. 2004-122114, Apr. 22, 2004, 1 page.

English Language Abstract, WO Patent First Publication No. 0122029, Mar. 29, 2001, 1 page (counterpart to KR 10-2001-0107968).

English Language Abstract, KR Patent First Publication No. 1020020088219, Nov. 27, 2002, 1 page.

English Language Abstract, KR Patent First Publication No. 1020030095813, Dec. 24, 2003, 1 page.

English Language Abstract, KR Patent First Publication No. 1020030096512, Dec. 31, 2003, 1 page.

English Language Abstract, KR Patent First Publication No. 1020040008966, Jan. 31, 2004, 1 page.

English Language Abstract, KR Patent First Publication No. 1020040057946, Jul. 2, 2004.

\* cited by examiner

SYSTEM AND METHOD FOR DETECTING DROPPING AMOUNT OF LIQUID CRYSTAL

CROSS-REFERENCE TO RELATED APPLICATION

This application claims priority to Korean Patent Application 10-2005-0003222 filed in the Korean Intellectual Property Office on Jan. 13, 2005, the entire content of which is incorporated herein by reference.

BACKGROUND OF THE INVENTION

1. Field of the Invention

The present invention is related to a system and method for monitoring a dropped amount of liquid crystal.

2. Description of the Related Art

Generally, a liquid crystal display (LCD) includes upper and lower display panels with electrodes formed thereon and a liquid crystal (LC) layer disposed between the upper and lower display panels. The upper and lower display panels are coupled with each other by a sealant and are supported by a spacer. As the LC molecules of the LC layer arrange themselves according to a voltage applied to the electrodes, an image is displayed by adjusting the voltage to control the transmittance of light through the LC layer.

As the LCD panels become larger, the method for forming the LC layer during the manufacturing of the LCD is evolving from the conventional process of injecting liquid crystal in a vacuum to dropping the liquid crystals on the panel.

The process of dropping an LC can be largely divided into three stages. In the first stage, a sealant is applied on a lower display panel to define a closed-loop active area. in the second stage, LC is dropped on the active area of the lower display panel. Then, the lower display panel is assembled with the upper display panel in vacuum and the sealant is hardened.

From a productivity standpoint, the process of dropping the LC is more advantageous than the LC injection method that is currently widely used.

However, since an assembly process is immediately performed in vacuum after the LC has been dropped, a defect may form in an active unfilled area (AUA) if the amount of the dropped LC is insufficient. If the amount of dropped LC is excessive, a defect may form as gaps near an edge.

The inner pressure in the gap between the assembled panels depends on the amount of the dropped LC. Accordingly, the LC should be dropped with an accuracy of a 1% error range to avoid defects. In order to accurately control the total amount of the dropped LC, the amount of the LC should be accurately monitored while the LC is being dropped. Furthermore, in order to maintain the inner pressure of the assembled panels at a predetermined level, the amount of the dropped LC is determined relative to the height of a column spacer. If the level of the dropped LC is higher than the column spacer, i.e., in the case that the amount of the dropped LC is more than a predetermined amount, a mura may be caused. On the other hand, if the amount of the dropped LC is less than the predetermined amount, an air bubble may form in the LC layer.

Since the exact amount of LC in a drop may vary, it is necessary to measure the amount of the LC being dropped on the active area at a regular time interval even if an LC dropper is accurately set up.

Currently, in order to accurately detect the amount of the LC being dropped on the active area, test amounts of LC is dropped on an electronic balance. In this case, a change in the amount of the LC being dropped on the active area can be minimized by shortening the measuring cycle.

Because the amount of the test LC is very small (e.g., about 1 to 4 mg), the test LC must be dropped more than 10 times in order to obtain sufficient accuracy with this test-amount method. An undesirable consequence of this repeated testing is that a substantial amount of the test LC is spent, increasing the test cost. Another problem with this test-amount method is that the weight and the deviation of the dropping LC are not the actual weight and deviation of one LC drop but an average value based on the weight and variation over several decades of the LC drops. Therefore, the accuracy is problematically deteriorated.

A method for accurately and cost-effectively measuring the amount of LC that is dropped onto a display panel is desired.

SUMMARY OF THE INVENTION

The present invention provides a system and method for measuring a dropping amount of a liquid crystal (LC) quickly and accurately.

In one aspect, the invention is a system that includes an LC dropper dropping an LC on a display panel and at least one LC detector detecting an amount of the LC while the LC is being dropped on the display panel. The LC detector includes a light source illuminating the LC that is dropping toward the display panel and a camera detecting a volume of the dropping LC by detecting the light passing through the dropping LC.

In one embodiment, the LC detector may be positioned between the LC dropper and the display panel. In another embodiment, a diffuser may be disposed at an output side of the light source. In yet another embodiment, the LC detector may be positioned above an upper portion of the LC dropper by a predetermined distance.

In some embodiments, a first light guide is disposed between the light source and the LC dropping on the display panel, and a second light guide is disposed between the dropping LC and the camera.

A diffuser may be disposed at an output side of the first light guide.

In another aspect, the system of the invention includes an LC dropper dropping a test LC on a test display panel, and at least one LC detector detecting an amount of the LC while the LC is being dropping on the test display panel. The LC detector comprises a light source illuminating the LC that is dropping toward the test display panel, and a camera for detecting a volume of the dropping LC by detecting a light passing through the LC.

In yet another aspect, the invention is a method for detecting an amount of LC in a drop. The method entails dropping an LC on a display panel, measuring a volume of the LC dropping on the display panel by at least one LC detector, and controlling an amount of the LC dropping from an LC dropper based on a feedback on the amount of the LC that is being dropped, which is calculated on the basis of the measured volume of the LC. The measuring of the volume of the LC dropping on the display panel includes illuminating the dropping LC with a light source of the LC detector, receiving the light from the light source with a camera, and determining the volume of the dropping LC using the received light.

BRIEF DESCRIPTION OF THE DRAWINGS

The present invention will become more apparent by describing preferred embodiments thereof in detail with reference to the accompanying drawings in which.

DETAILED DESCRIPTION OF THE PREFERRED EMBODIMENTS

With reference to the accompanying drawings, the present invention will be described in order for those skilled in the art to be able to implement the invention.

The embodiments described herein may be modified in various ways without departing from the spirit or scope of the present invention.

A system and a method for measuring the amount of a dropping LC according to an embodiment of the present invention will hereinafter be described in detail with reference to the accompanying drawings.

Figure 1:
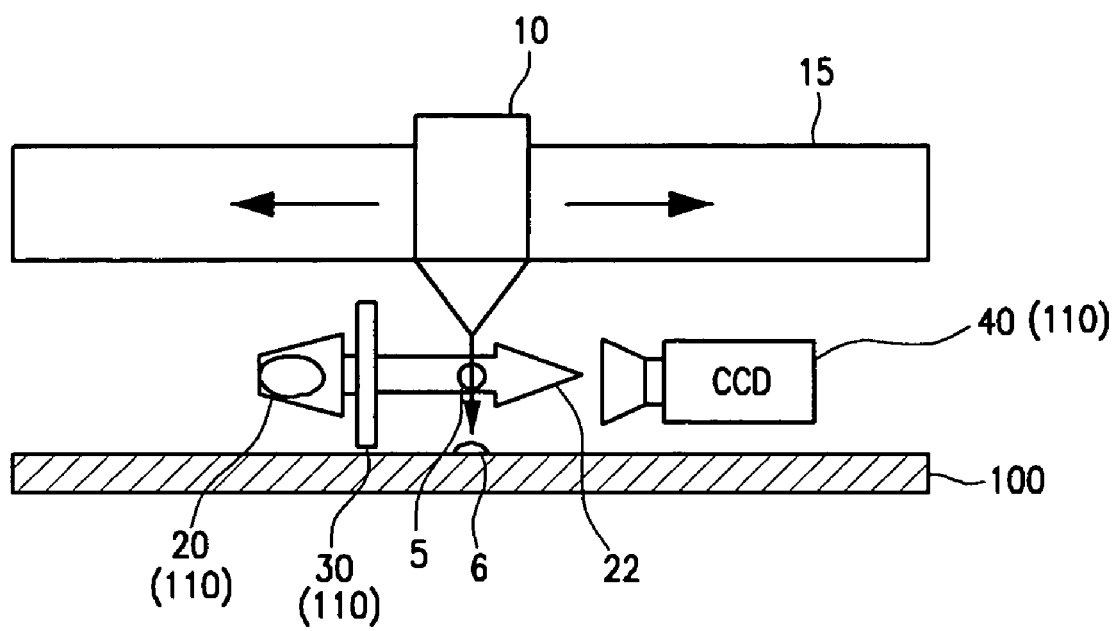
FIG. 1 shows a system for detecting an amount of an LC according to an embodiment of the present invention.
Figure 2:
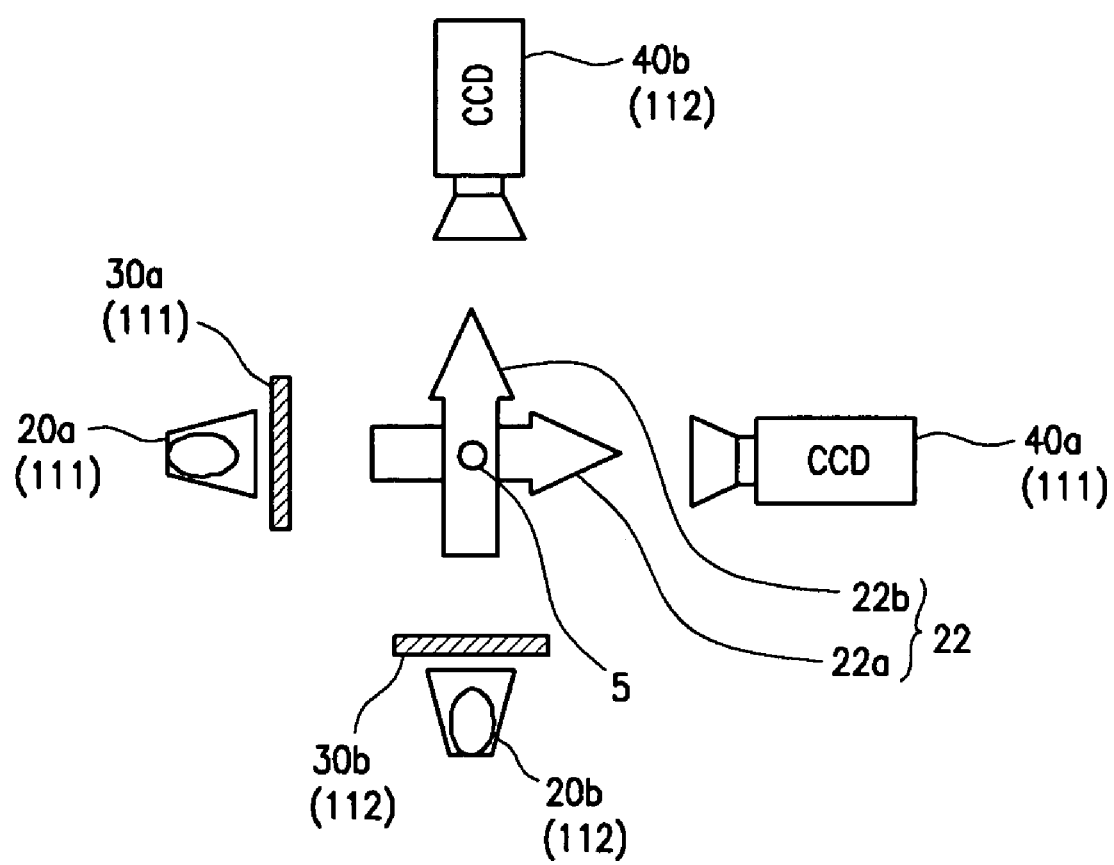
FIG. 2 shows an arrangement a systems for detecting an amount of an LC according to a second embodiment of the present invention.

FIG. 1 shows a system for detecting the amount of LC according to an embodiment of the present invention, and FIG. 2 shows an arrangement of a plurality of the systems for detecting the amount of LC according to another embodiment of the present invention.

As shown in FIG. 1, a system for detecting the amount of LC according to an embodiment of the present invention includes an LC dropper 10 dropping the LC 5 on a display panel 100 and an LC detector 110 detecting the amount of the LC being dropped.

The LC dropper 10 is mounted on a position controlling device 15 and is moved by the position controlling device 15 above the display panel 100 so as to drop an LC 6 on a predetermined location on the display panel 100.

The LC detector 110 includes a light source 20 shining light onto the LC 5 that is being dropped on the display panel 100 and a camera 40 measuring a volume of the LC 5 by detecting the light that passes through the LC 5.

The camera 40 optically detects the volume of the rapidly dropping LC 5 by utilizing a high speed charge coupled device (CCD).

A diffuser 30 is disposed at an output side of the light source 20 where the light 22 is output, dispersing the light 22 such that it illuminates the LC 5 more widely. In addition, the diffuser 30 enables the camera 40 to better receive the light 22 that passes through the dropping LC 5.

Pictures of one LC 5 dropped from the LC dropper 10 are taken by the CCD camera 40, and they are used for determining the volume of the LC 5. The LC 5 is dropped from the LC dropper 10 so that each drop weighs about 2 mg. While the drop of LC 5 is traveling to the display panel 100, the CCD camera 40 can take more than 10 pictures for the volume of the drop of LC 5. Taking the pictures at rapid intervals improves the accuracy of the volume calculation for the LC.

Because the drop of LC 5 is not perfectly spherical in shape, the accuracy in measuring the amount of the LC in a drop may be enhanced by calculating an average value from a plurality of pictures.

The LC detector 110 is positioned between the LC dropper 10 and the display panel 100.

The camera 40 measures the actual volume of the LC 5 being dropped during an actual manufacturing process. Then, the LC dropper 10 can control the amount of the subsequent drop(s) of LC according to a real-time feedback about the amount of the LC that is already dropped, which is calculated on the basis of the actual volume of the LC 5. This way, the LC dropper 10 controls the total volume of the LC that is dropped on the display panel 100.

With the method of the invention, additional apparatus and process for detecting the amount of the dropping LC, such as an electronic balance or a weight measurement device, are not necessary. Thus, manufacturing cost is reduced and a quick feedback can be realized.

In addition, because not much LC is wasted and the detection interval may be shortened, the method of the invention provides improved accuracy for dropping an LC.

Furthermore, the system for detecting the amount of dropping LC according to an embodiment of the present invention measures the amount of the dropping LC based on the volume of each LC drop, not based on the weights of multiple LC drops. Therefore, any deviation in the amount of the dropping LC is accurately calculated and compensated, and the amount of the dropping LC is not affected by its specific gravity.

A method for detecting the amount of dropping LC utilizing the above-described system is described hereinafter.

First, a drop of LC is placed on a display panel 100. Then, a volume of the dropping LC is detected by the LC detector 110. While the LC is dropping, the volume of the LC is determined by the camera 40, which detects the amount of light from the light source 20 of the LC detector 110 that passes through the dropping LC 5.

The amount of the dropping LC is calculated based on the detected volume of the LC. Subsequently, the amount of the LC to be dropped is controlled based on a feedback of the calculated amount of the LC that was dropped onto the panel 100.

As shown in FIG. 2, the volume of the LC can be detected by a plurality of LC detectors. The plurality of the LC detectors include a first LC detector 111 and a second LC detector 112. The first LC detector 111 includes a light source 20a and a camera 40a and the second LC detector 112 includes a light source 20b and a camera 40b.

A plurality of light beams 22a and 22b are emitted from the light source 20a and 20b, and a plurality of diffusers 30a and 30b are positioned in front of the light sources 20a and 20b. Taking pictures of the LC drop from different angles with the plurality of cameras 40a, 40b improves the accuracy in determining the volume of the LC.

Figure 3:
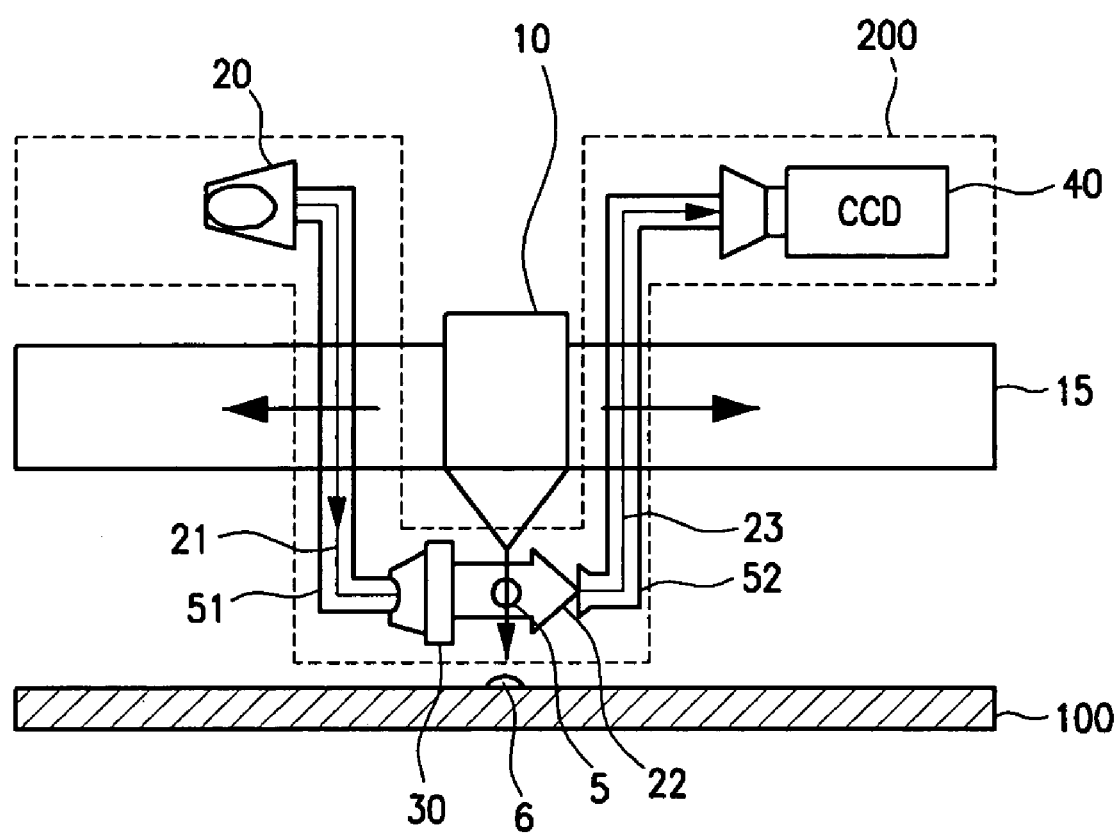
FIG. 3 shows a system for detecting an amount of an LC according to another embodiment of the present invention.

FIG. 3 illustrates a system for detecting an amount of an LC according to another embodiment of the present invention. This embodiment reduces or prevents contamination of the components from dust or foreign substances.

As shown in FIG. 3, the system for detecting the amount of the LC according to an embodiment of the present invention includes the LC dropper 10 and an LC detector 200.

The LC dropper 10 is mounted on a position controlling device 15 and is moved above the display panel 100 so as to drop an LC 6 on a predetermined location of the display panel 100.

The LC detector 200 includes a light source 20 shining light onto a dropping LC 5 and a camera 40 that measures the volume of the LC 5 based on the light from the light source 20 that passes through the LC 5. If the LC dropper or the LC detector is located close to the display panel, dust or foreign substances tend to fall on the dropping LC and the display panel 100. Because the light source 20 and the camera 40 of the LC detector 200 are positioned above the upper portion of the LC dropper 10 by a predetermined distance, the amount of dust or foreign substances that fall on the dropped LC 6 is reduced.

In this embodiment, the light source 20 and the camera 40 are disposed on the position controlling device 15.

A first light guide 51 is disposed between the light source 20 and the dropping LC 5, and a second light guide 52 is disposed between the dropping LC 5 and the camera 40, such that the light source 20 may illuminate the dropping LC 5 and the camera may receive the light passing through the LC 5.

The camera 40 optically detects the volume of the LC 5 drop by utilizing a charge coupled device (CCD).

The diffuser 30 is disposed near an output end of the first light guide 51 and receives the light emitted from the light source 20. By diffusing the light, the diffuser 30 allows the light to illuminate the LC 5 more broadly. In addition, the diffuser 30 enables the camera 40 to better receive the light 22 and 23 that pass through the dropping LC 5.

Multiple pictures of one LC dropped from the LC dropper 10 are taken by the CCD camera 40, and at least one such picture of the one LC 5 is used to determine the volume of the LC 5.

A drop of LC 5 that is dropped from the LC dropper 10 weighs about 2 mg. While the drop of LC 5 is traveling to the display panel 100, the CCD camera 40 can take more than 10 pictures of the LC 5. Taking the pictures at rapid intervals improves the accuracy of the volume calculation for the LC.

Because the drop of LC 5 is not perfectly spherical, the accuracy in measuring the amount of LC in a drop may be enhanced by calculating an average of data detected from a plurality of pictures.

The LC detector 200 determines an actual volume of the LC 5 during an actual manufacturing process. Then, the LC dropper 10 controls the amount of the LC in subsequent drops according to a real time feedback based on the actual volume of the LC 5 that was dropped.

The LC dropper 10 controls the volume of the LC dropped on the display panel 100 during the actual manufacturing process. By eliminating the need for additional apparatus and process such as an electronic balance or weight detection, the invention reduces manufacturing costs. The invention also has the benefit of a quick feedback on the LC volume. In addition, because LC is not consumed wastefully and the detection interval may be shortened, the accuracy of LC volume measurement is enhanced.

Furthermore, the system for detecting the amount of a dropping LC according to an embodiment of the present invention measures the amount of the dropping LC based not on the volume of each LC drop, not based on the weights of multiple LC drops. Therefore, any deviation in the amount of the dropping LC is accurately calculated and compensated, and the amount of the dropping LC is not affected by its specific gravity.

Figure 4A:
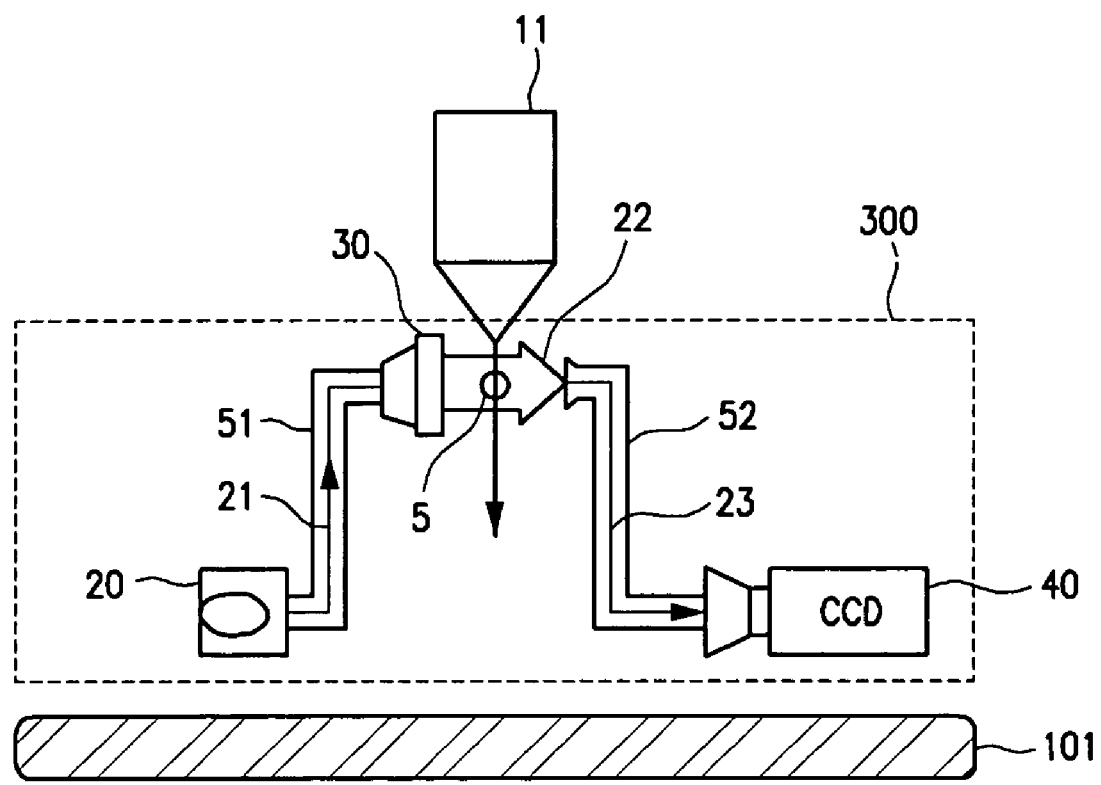
FIG. 4A and FIG. 4B show a system for detecting an amount of an LC according to still another embodiment of the present invention.
Figure 4B:
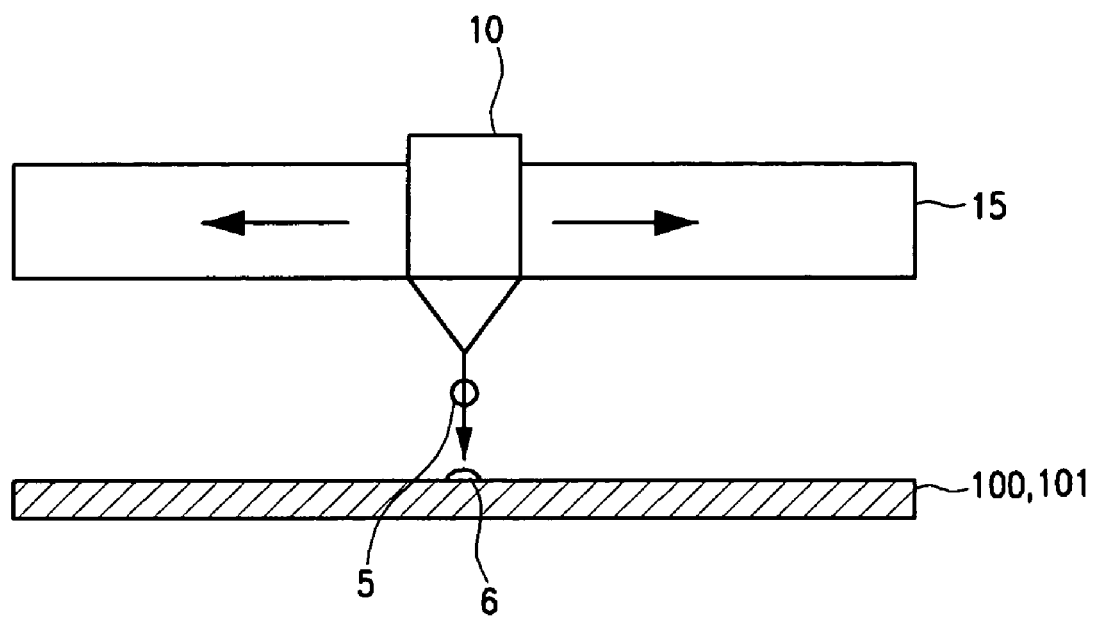

FIGS. 4A and 4B illustrates a configuration for a case where reduction of contamination from dusts or foreign substances is highly desired. That is, FIG. 4A and FIG. 4B shows a system for detecting an amount of LC according to another embodiment of the present invention.

As shown in FIG. 4A, a system for detecting the amount of LC includes a test LC dropper 11 dropping the LC 5 on a test display panel 101 and an LC detector 300 detecting a amount of the dropping test LC.

The test LC dropper 11 is located outside of the test display panel 101 on which a real LC dropping process is performed and the test LC dropper 11 drops the test LC 5.

The LC detector 300 includes a light source 20 shining light onto the drop of LC 5 that is being dropped on the test display panel 101 and a camera 40 measuring a volume of LC 5 by detecting the light that has passes through the LC 5. If the LC dropper or the LC detector is located close to the display panel, the dust or the foreign substances tend to fall on a dropping LC and a display panel.

However, because the test LC dropper 11 and the LC amount detector 300 are located outside of the display panel 101 on which a real LC dropping process is performed, the risk of dust or foreign substances contaminating the dropping LC 6 and the display panel 100 is reduced.

A first light guide 51 is disposed between the light source 20 and the dropping LC 5, and a second light guide 52 is disposed between the dropping LC 5 and the camera 40, such that the light source 20 may illuminate the dropping LC 5 and the camera may receive the light passing through the LC 5.

The camera 40 optically detects the volume of the LC 5 drop by utilizing a charge coupled device (CCD).

The diffuser 30 is disposed near an output end of the first light guide 51 and receives the light emitted from the light source 20. By diffusing the light, the diffuser 30 allows the light to illuminate the LC 5 more broadly. In addition, the diffuser 30 enables the camera 40 to better receive the light 22 and 23 that pass through the dropping LC 5.

As shown in FIG. 4B, an LC dropper 10 drops the LC on the display panel 100/101 by an amount that is adjusted according to the measured amount of the LC that has already been dropped.

The LC dropper 10 is positioned with the controlling device 15 and is moved above the display panel 100 so as to drop an LC 6 on a predetermined location on the display panel 100.

According to the system and method for determining the amount of LC in a drop of LC, the amount can be controlled according to a real-time feedback on the dropped amount of the LC as detected by a CCD camera.

Because additional apparatus and process for detecting the amount of the dropping LC are not necessary, manufacturing costs are reduced. The quick feedback on the amount of LC that is needed further reduces cost by preventing wasteful use of LC. In addition, because LC is not consumed wastefully and the detection interval may be shortened, accuracy of dropping an LC may be enhanced.

Furthermore, as stated above, the amount of the dropping LC is detected based on the volume of each LC drop, not on the weights of a plurality of the dropping LC. Therefore, any deviation in the amount of the dropping LC is accurately calculated, and the amount of the dropping LC is not affected by its specific gravity.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A system for detecting an amount of an LC comprising:
   an LC dropper dropping an LC on a display panel; and
   at least one LC detector detecting an amount of the LC while the LC is being dropped on the display panel, wherein the LC detector includes:
   a plurality of light sources illuminating the LC that is dropping toward the display panel; and
   a camera detecting a volume of the dropping LC by detecting the light passing through the dropping LC.

2. The system of claim 1, wherein the LC detector is positioned at a height between the LC dropper and the display panel.

3. The system of claim 2, wherein a diffuser is disposed at an output side of the light source.

4. The system of claim 1, wherein the LC detector is positioned above the LC dropper by a predetermined distance.

5. The system of claim 4, wherein a first light guide is disposed between one of the light sources and the LC dropping on the display panel, and a second light guide is disposed between the dropping LC and the camera.

6. The system of claim 5, wherein a diffuser is disposed at an output side of the first light guide.

7. A system for detecting an amount of an LC comprising:
   an LC dropper dropping a test LC on a test display panel; and
   at least one LC detector for detecting an amount of the LC while the LC is being dropped on the test display panel, wherein the LC detector includes:
   a plurality of light sources illuminating the LC that is dropping toward the test display panel; and
   a camera detecting a volume of the dropping LC by detecting a light passing through the LC.

8. The system of claim 7, wherein the LC amount detector is positioned outside of the test display panel.

9. A method for detecting an amount of a dropping LC comprising:
   dropping an LC on a display panel;
   measuring a volume of the LC dropping on the display panel by at least one LC detector; and
   controlling an amount of the LC dropping from an LC dropper based on a feedback on the amount of the LC that is being dropped, which is calculated on the basis of the measured volume of the LC,
   wherein the measuring of the volume of the LC dropping on the display panel includes:
   illuminating the dropping LC with a plurality of light sources of the LC detector;
   receiving the light from at least one of the light sources with a camera; and
   determining the volume of the dropping LC using the received light.

10. The method of claim 9, wherein the LC that is being dropped is positioned between the light sources and the camera such that the camera receives light that passes through the LC that is being dropped.

11. A system for detecting an amount of an LC comprising:
    an LC dropper dropping an LC on a display panel; and
    a plurality of LC detectors detecting an amount of the LC while the LC is being dropped on the display panel, wherein each of the LC detectors includes:
    a light source illuminating the LC that is dropping toward the display panel; and
    a camera detecting a volume of the dropping LC by detecting light passing through the dropping LC.

* * * * *